(12) United States Patent
Brankov et al.

(10) Patent No.: US 11,576,636 B2
(45) Date of Patent: Feb. 14, 2023

(54) APPARATUS AND METHOD FOR ANALYZER-BASED CONTRAST IMAGING WITH A POLYCHROMATIC BEAM

(71) Applicants: Jovan G. Brankov, Evanston, IL (US); Oriol Caudevilla Torras, Seattle, WA (US); Wei Zhou, Aurora, IL (US)

(72) Inventors: Jovan G. Brankov, Evanston, IL (US); Oriol Caudevilla Torras, Seattle, WA (US); Wei Zhou, Aurora, IL (US)

(73) Assignee: ILLINOIS INSTITUTE OF TECHNOLOGY, Chicago, IL (US)

( * ) Notice: Subject to any disclaimer, the term of this patent is extended or adjusted under 35 U.S.C. 154(b) by 176 days.

(21) Appl. No.: 16/867,662

(22) Filed: May 6, 2020

(65) Prior Publication Data

US 2020/0352533 A1 Nov. 12, 2020

Related U.S. Application Data

(60) Provisional application No. 62/846,226, filed on May 10, 2019.

(51) Int. Cl.
*A61B 6/00* (2006.01)

(52) U.S. Cl.
CPC ............ *A61B 6/484* (2013.01); *A61B 6/4092* (2013.01); *A61B 6/463* (2013.01); *A61B 6/483* (2013.01); *A61B 6/502* (2013.01); *A61B 6/5205* (2013.01)

(58) Field of Classification Search
CPC ......... A61B 6/00; A61B 6/484; A61B 6/4092; A61B 6/502; A61B 6/5205; A61B 6/483; A61B 6/463
See application file for complete search history.

(56) References Cited

U.S. PATENT DOCUMENTS

| | | | |
|---|---|---|---|
| 5,509,043 | A | 4/1996 | Van Der Sluis |
| 5,987,095 | A | 11/1999 | Chapman et al. |
| 6,947,521 | B2 | 9/2005 | Wernick et al. |
| 7,469,037 | B2 | 12/2008 | Wernick et al. |
| 2006/0072702 | A1 | 4/2006 | Chapman |
| 2007/0291896 | A1 | 12/2007 | Parham et al. |
| 2009/0060134 | A1 | 3/2009 | Fuller |
| 2015/0226685 | A1 | 8/2015 | Connor |

OTHER PUBLICATIONS

U.S. Patent Office, English language version of the International Search Report, Form PCT/ISA/210 for International Application PCT/US2020/032020, dated Aug. 6, 2020 (3 pages).
U.S. Patent Office, English language version of the Written Opinion of the ISA, Form PCT/ISA/237 for International Application PCT/US2020/032020, dated Aug. 6, 2020 (8 pages).

*Primary Examiner* — Jurie Yun
(74) *Attorney, Agent, or Firm* — Pauley Erickson & Swanson (57) ABSTRACT

A method and system for detecting an image of an object in an analyzer-based system with a polychromatic x-ray beam from an x-ray source, wherein an analyzer crystal and a detector simultaneously acquire a rocking curve of the x-ray beam for all energies of the x-ray beam. The x-ray beam is diffracted through the object using an asymmetrical monochromator. A detector movement is synchronized with one of the x-ray source or the object. The synchronization includes moving the detector at a first rate that is different than a second rate of the object or the x-ray source, wherein a ratio between the first rate and the second rate is determined by the magnification of the system.

21 Claims, 6 Drawing Sheets

APPARATUS AND METHOD FOR ANALYZER-BASED CONTRAST IMAGING WITH A POLYCHROMATIC BEAM

CROSS REFERENCE TO RELATED APPLICATION

This application claims the benefit of U.S. provisional application, Ser. No. 62/846,226, filed on 10 May 2019. The provisional application is hereby incorporated by reference herein in its entirety and is made a part hereof, including but not limited to those portions which specifically appear hereinafter.

STATEMENT REGARDING FEDERALLY SPONSORED RESEARCH

This invention was made with government support under R01EB023969 awarded by National Institute of Health (NIH)/NIBIB. The government has certain rights in the invention.

FIELD OF THE INVENTION

This invention relates generally to the field of X-ray imaging, and more particularly, to an apparatus, system, and method for performing phase contrast imaging using sources (e.g., X-ray tubes). The invention further relates to an apparatus, system, and method for analyzer-based phase-contrast imaging using polychromatic beams.

BACKGROUND OF THE INVENTION

Phase contrast imaging (PCI) is increasingly being considered as an alternative to conventional X-ray imaging. For example, due to its extreme contrast when imaging soft tissue, PCI has the potential to reduce the alarming number of false positives reported in preventive mammography. Additionally, PCI has potential to decrease the deposited glandular dose in the tissue. In particular, analyzer-based imaging (ABI) is one of the methods to obtain PCI images. It has been used to obtain remarkable contrast images of breast tissue (as well as other soft tissue like ligament and muscle) using synchrotron light as well as in compact setups. Ultimately, ABI mammography could improve the quality of current breast imaging technologies while, at the same time, reducing their risks.

ABI can provide three parametric images: an absorption image, a refraction image, and an ultra-small angle scatter image. The absorption image is similar to a digital mammogram. However, ABI completely rejects Compton scatter, producing sharper absorption images compared to current mammography systems. The refraction image is an estimation of the very small deflections in the photon paths produced by small changes in the tissue's density. Finally, the ultra-small angle scatter image measures the dispersive properties of sub-pixel textural components in the tissue.

ABI systems use two or more crystals as very selective angular filters to study the changes in the angular content of the beam when it reacts to the imaged sample. Such crystals are called the monochromator and analyzer, and are commonly made of Silicon (Si) or Germanium (Ge). By rotating the analyzer, the system acquires samples of the Angular Intensity Profile (AIP) of the beam, known as angular images. Angular data is used to retrieve absorption, refraction, and scatter images.

Figure 1:
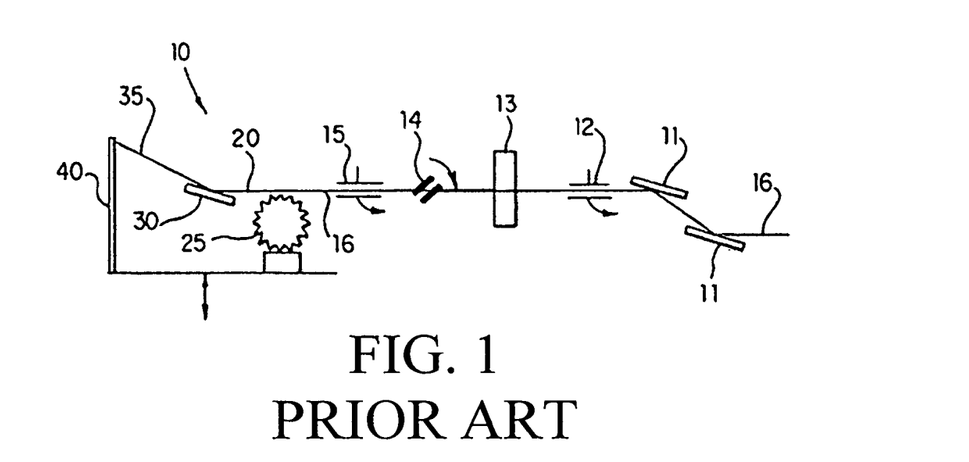
FIG. 1 is a prior art analyzer-based imaging system.

Diffraction Enhanced Imaging (DEI) and Multiple Image Radiography (MIR) are the earliest and most common approaches. FIG. 1 shows a schematic diagram of analyzer system 10, according to the DEI method and system of U.S. Pat. No. 5,987,095, herein incorporated by reference. Crystal analyzer 30 represents a Bragg type crystal analyzer. A double crystal monochromator 11 is used to generate monoenergetic x-ray beam 16. Each crystal of monochromator 11 is constructed of silicon using a (3, 3, 3) lattice planes structure. The lattice planes used in monochromator 11 match those used in crystal analyzer 30. Shutter 14, such as a rotary shutter or the like, can be used to control exposure and limit unnecessary scatter of the beam. A detector is used to detect an image of object 25. In one preferred embodiment according to this invention, the object 25 image is detected with image plate 40 which comprises a photostimulable phosphor image plate typically used for radiology. An image recorded on image plate 40 can be digitized, stored, and displayed.

Object 25 and image plate 40 can be scanned together, such as in a direction shown by the vertical arrow in FIG. 1, to provide a two-dimensional radiograph. Ionization chamber 12 can be used downstream of monochromator 11, for example to monitor tuning. Ionization chamber 15, as shown in FIG. 1, which is positioned upstream of object 25, can be used to monitor a radiation dose at a surface of object 25.

Figure 2:
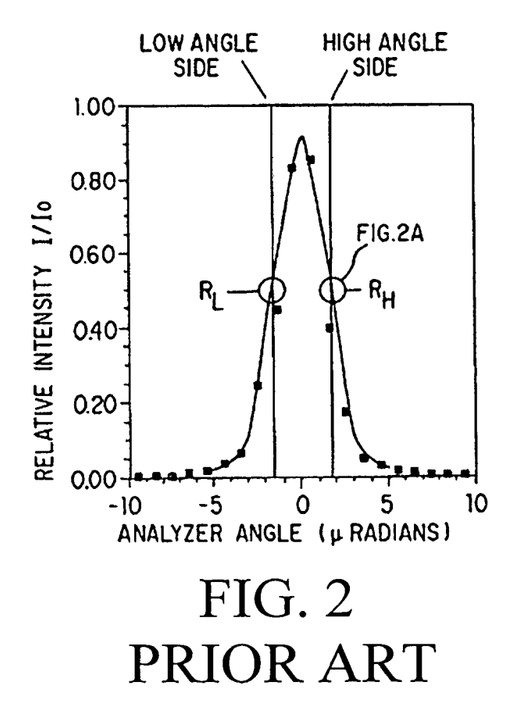
FIG. 2 is an exemplary rocking curve of the system of FIG. 1.
Figure 2A:
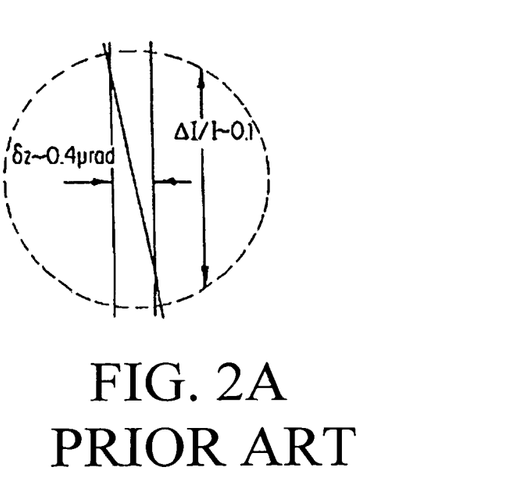
FIG. 2A is an exploded portion of FIG. 2.

Crystal analyzer 30 is positioned between object 25 and image plate 40. Crystal analyzer 30 is fixed spatially with respect to transmitted beam 20, oriented to diffract transmitted beam 20 onto image plate 40. Fine angular control of crystal analyzer 30 can position crystal analyzer 30 at various positions within the rocking curve shown in FIG. 2. FIG. 2 shows a solid line curve representing a theoretical calculation of the rocking curve for crystal analyzer 30. Such theoretical calculation includes effects of x-ray beam 16, as prepared by double crystal monochromator 11. The points on the curve of FIG. 2 represent representative measured points of the rocking curve of crystal analyzer 30. FIG. 2 shows the low angle side and the high angle side of the rocking curve, which are preferably the locations at which two images are detected.

The crystal diffracts incoming light traveling within a very narrow angular range, the center of which is known as Bragg's angle $\theta_B$. Bragg's angle is energy dependent and can be computed using Bragg's Law:

$$\lambda m = 2d \sin \theta_B \qquad (1)$$

$$\lambda = \frac{12.383}{E}$$

where E and $\lambda$ are the energy and wavelength of the radiation, m is an integer, and d is the spacing between atomic layers within the crystalline structure. The angular acceptance range is known as Darwin width, which is in the μrad range. For example, Si111 and Ge111 have Darwin widths of 4.31 and 10.47, μrad at 59.32 keV, respectively.

Since Bragg's law is energy dependent, previous work in ABI assumed quasi-monochromatic light to be indispensable to obtain meaningful images. Unfortunately, quasi-monochromatic radiation must be obtained by conditioning the beam with the monochromator. Hence, the monochromator absorbs most of the radiation produced by the X-ray source narrowing its energy spectrum. This process causes very few photons to reach the object and detector. As a consequence, the exposure time needed for ABI is currently a limiting factor for its implementation in a clinical setup. After the monochromator, the resulting beam is also narrow in the vertical direction and close to a fan beam in the horizontal direction. Because of that, the conditioned beam has a very wide aspect ratio: typically a few millimeters high versus several centimeters wide. Given this geometry, the samples need to be scanned vertically.

Since exposure times are often the limiting factors in ABI systems, synchrotron light sources (SLS) were instrumental during the early stages of ABI research. Under synchrotron light conditions, the number of photons is high enough to produce low-noise images with a reasonable exposure time, even after conditioning the beam. Using SLS, a number of publications set up the foundations of analyzer-based imaging.

In the recent years, some groups have tried to transition to a compact setup capable of imaging a breast sample in a practical time for clinical applications using conventional x-ray sources (CXS). Inspired by synchrotron research, all previous efforts have been focused on obtaining bright enough near-monochromatic beams by capturing the emission line of a CXS. Despite these efforts compact ABI systems remain to be limited by the long exposure times required for imaging.

Therefore, there is a need for systems and methods for performing X-ray phase contrast imaging using a conventional X-ray source and polychromatic beams, instead of SLS or CXS with quasi-monochromatic light(s), with lower cost and sufficient power density to provide high resolution medical images and shortened exposure times required for imaging.

SUMMARY OF THE INVENTION

A general object of this invention is to provide an apparatus, system, and method for performing X-ray phase contrast imaging using conventional X-ray sources, such as polychromatic beams. The present invention provides an apparatus, system, and method for performing analyzer-based imaging with wide-spectrum beams instead of synchrotron light sources or quasi-monochromatic light sources. The method of this invention allows for compact imaging systems, such as having distances between the source and detector of 1.5 meters or less.

Embodiments of this invention include methods of and systems for X-ray analyzer-based imaging using polychromatic beams, including: an X-ray source with polychromatic beams, a monochromator that intercepts X-ray beams generated from the X-ray source and irradiates an object, and an analyzer that receives the beams passing through the object, and a detecting system. The analyzer is positioned specifically for acquiring the multiple energies of the polychromatic rocking curve simultaneously, and the detecting system detects an image of the object from the beams diffracted from the analyzer.

Embodiments of the invention include using a single or multiple crystal(s) as the monochromator, such single or multiple crystal system has no theoretical limitation on the crystal size, for example, silicon pieces with a diameter of around 28 cm can be used for producing wider beams and reducing required exposure time. As used herein "monochromator" refers to conditioning crystals and is not required to transmit a narrower band of wavelengths of light or other radiation chosen from input of a wider range of wavelengths. "Monochromator" is used in description of this invention for easier understanding due to its wide usage in industry. As asymmetrical plane crystal monochromator is preferred in many embodiments of this invention.

The invention includes a method for detecting an image of an object in an analyzer-based system with a polychromatic x-ray beam from an x-ray source, wherein an analyzer crystal and a detector simultaneously acquire a rocking curve of the x-ray beam for all energies of the x-ray beam, the method including synchronizing a detector movement with one of the x-ray source or the object. As used herein "detector movement" refers to or includes either a physical movement of the detector or a frame movement technology, such as Time-Delay Integration (TDI) or equivalent. In embodiments of this invention, the synchronizing includes a detector movement at a first rate that is different than a second rate of the object or the x-ray source, wherein a ratio between the first rate and the second rate is determined by the magnification of the system. The first rate is desirably, but not necessarily, faster than the second rate of the object or the x-ray source. The images taken during the movement are aligned at the detector as a function of a ratio of the first rate to the second rate to provide the final image. Adjusting the first rate and/or second rate can improve a resolution of the final image of the object.

In embodiments of this invention, the ratio of the first rate to the second rate is a function of a vertical magnification of the particular analyzer-based system. The vertical magnification is a function of (e.g., a mathematical relationship between) a crystal plane of the monochromator, a first distance between the x-ray source and a leading edge of the monochromator, a second distance extending from the leading edge to the object, and a third distance extending from the object to the detector.

The invention further includes a method for detecting an image of an object in an analyzer-based system, including the steps of: generating a polychromic x-ray beam from an x-ray source; diffracting the x-ray beam by a monochromator; transmitting the x-ray beam through the object and emitting from the object a transmitted beam; directing the transmitted beam off a crystal analyzer to a detector; synchronizing a movement of the object or the x-ray source with a detector movement during the transmitting; detecting more than one image of the object at the detector during the synchronizing; and combining the more than one image to derive the image of the object.

The present invention provides methods for performing X-ray phase contrast imaging using polychromatic beams, including: generating X-ray with polychromatic beams, intercepting the beams with a monochromator, irradiating an object with such transmitted beam from monochromator and directing the beam to an analyzer, modulation and adjusting the analyzer position for acquiring the polychromatic rocking curve simultaneously, computing a DEI estimator using such experimentally measured polychromatic rocking curve, measuring the weighted average of the attenuation and refraction across the source's energy range, evaluating the spatial blurring and magnification properties of the system, and obtaining the reconstructed image for the object.

In embodiments of this invention, expressions of the images are derived from reconstruction with DEI using polychromatic light(s), such expressions are weighted average across the accepted images. Spatial blurring and magnification properties of ABI systems using polychromatic beams are derived and evaluated.

Embodiments of the invention include apparatus, systems, and methods of obtaining image(s) of objects with broad-spectrum Bremsstrahlung radiation (with or without characteristic L or K lines), which demonstrates the feasibility of polychromatic imaging under 100 micron resolution.

Other objects and advantages will be apparent to those skilled in the art from the following detailed description taken in conjunction with the appended claims and drawings.

DETAILED DESCRIPTION OF THE INVENTION

The present invention provides methods, apparatuses, and systems for performing X-ray analyzer-based imaging using polychromatic beams.

Figure 3:
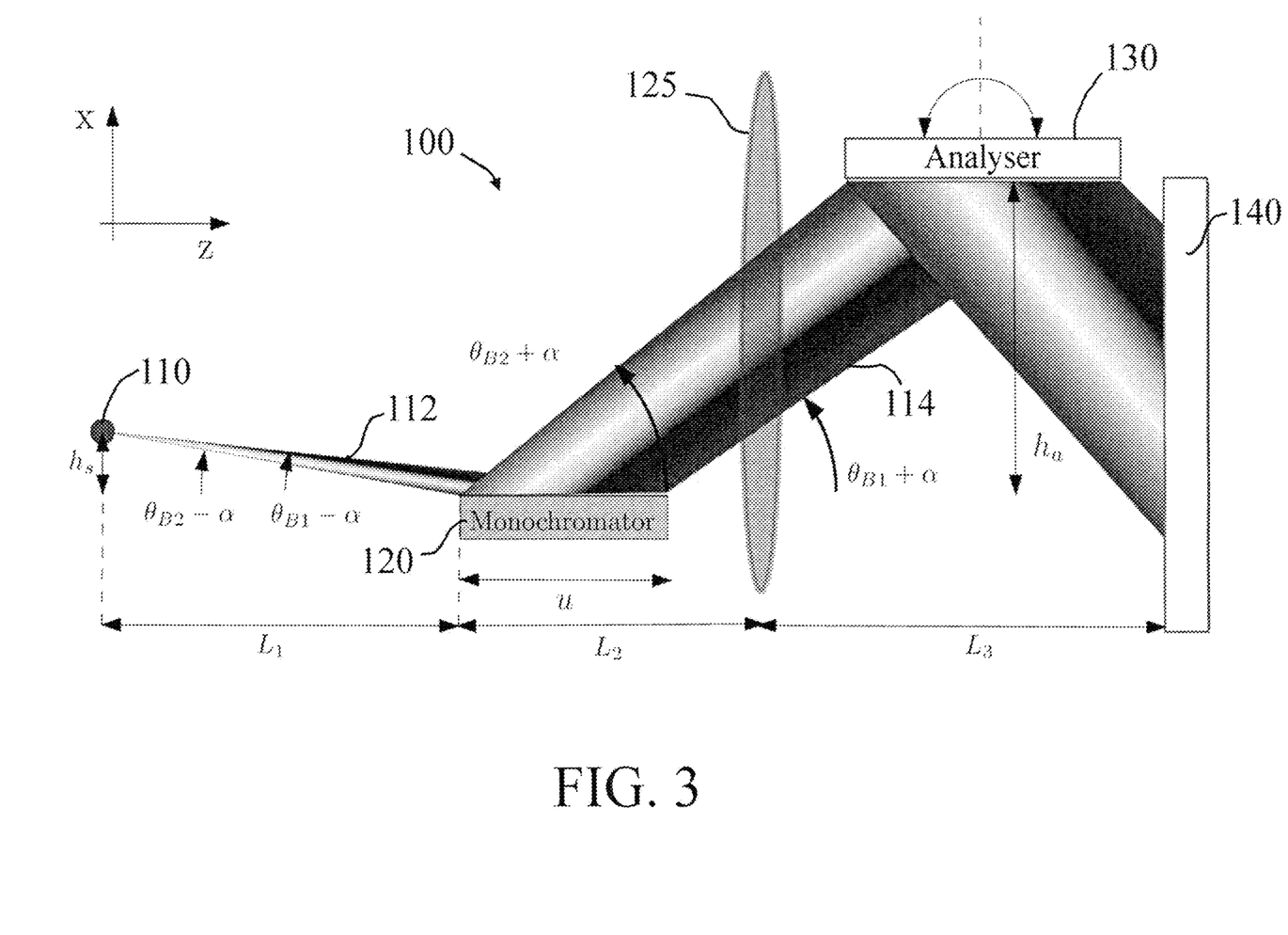
FIG. 3 is a schematic illustration of a polychromatic beam in an analyzer-based imaging system according to one embodiment of this invention.

FIG. 3 schematically illustrates an analyzer-based system 100 with a polychromatic x-ray source 110, according to one embodiment of this invention. The source 110 generates a polychromic x-ray beam 112. The x-ray beam 112 is diffracted by the monochromator 120, and then transmitted through the object 125, emitting a transmitted beam 114. The x-ray beam 112 and/or transmitted beam 114 is desirably a slot beam, having a narrow width relative to the longitudinal length. The transmitted beam is directed off a crystal analyzer 130 to a detector 140. The analyzer crystal 130 and the detector 140 simultaneously acquire a rocking curve of the x-ray beam for all energies of the x-ray beam. The object is desirably on an object support or holder. The detector is desirably moved, either physically or with frame movement technology (e.g., TDI), along the narrow axis of the x-ray slot beam, or perpendicular to the longitudinal axis of the x-ray slot beam.

Methods and systems of this invention allow for using polychromatic x-ray beams, while providing a compact system. In embodiments of this invention, the distance between the x-ray source and the detector is less than 5 meters, desirably about 2 meters or less, and preferably about 1.5 meters or less, thereby facilitating use in medical treatment spaces. The X-ray source power is desirably at least 1.2 kW, and preferably 12 kW.

In embodiments of this invention, the problems of using polychromatic x-ray beams in analyzer-based systems is mitigated by synchronizing a detector movement with the x-ray source and/or the object. The synchronized movement is based upon mathematical relations and/or positions of these components within a particular system. In embodiments of this invention, the synchronizing includes moving the detector at a first rate that is different than a second rate of the object and/or the x-ray source. The ratio between the first rate and the second rate can be determined by the magnification of the system, such as the vertical magnification of the system. As such, adjusting the first rate and/or second rate can be used to improve a resolution of the image of the object. In currently preferred embodiments, the synchronizing includes moving the detector at a first rate that is faster than a second rate of the object or the x-ray source. Embodiments of this invention allow for polychromatic x-ray sources by using an asymmetrical monochromator.

Crystal materials, such as Si and Ge, are the key elements in ABI systems. When illuminated with X-rays, each atom within their crystalline structure produces scattered radiation. However, the superposition of all scattered light produced by the atoms is not always constructive. Depending on the internal spacing of atomic layers, the energy of the radiation and the direction of propagation, the light can be absorbed or reflected by the crystal. Bragg's law (Eq. 1) establishes the relationship between the energy and the angle of total reflection.

Additionally, Darwin's dynamical theory studies the reflectivity of semiconducting crystals for directions other than Bragg's angle. Darwin's theory shows that small deviations of Bragg's condition also provide total reflection while the crystal absorbs almost completely the radiation otherwise. Ultimately, the reflectivity curve of perfect crystals is:

$$r(x_c) = \begin{cases} x_c - \sqrt{x_c^2 - 1} & 1 \leq \text{Re}\{x_c\} \\ x_c - i\sqrt{1 - x_c^2} & -1 \leq \text{Re}\{x_c\} \leq 1 \\ x_c + \sqrt{x_c^2 - 1} & \text{Re}\{x_c\} \leq 1 \end{cases} \quad (2)$$

where the normalized variable $x_c$ relates to the incident angle through the equation $$\theta = x_c \, \text{Re}\left\{\frac{g}{m\pi}\right\} \tan \theta_B + \theta_B \quad (3)$$

and the complex value g depends on the crystal's crystalline structure and the energy of the X-rays. Due to equations (2) and (3), the reflectivity depends on the angle and the energy of the radiation. Hence, the Darwin's curve of a crystal is defined as:

$$r(\theta, E) = |r(x_c(\theta, E))|.$$

In order to accept more photons in ABI systems, crystal surfaces can be polished to form an angle α with respect to the atomic layers of the material. Asymmetric crystals present a different incoming and outgoing Darwin curve:

$$r_i(\theta, E) = r(\sqrt{b}^{-1}(\theta - \theta_B + \alpha) + \theta_B, E)$$

$$r_o(\theta, E) = r(\sqrt{b}(\theta - \theta_B + \alpha) + \theta_B, E) \quad (4)$$

where b is the asymmetric factor:

$$b = \frac{\sin(\alpha + \theta_B)}{\sin(\alpha - \theta_B)} \quad (5)$$

As a consequence of equation (4), asymmetric crystal reflections are non-specular. Input and output angles are different:

$$\theta_i = \theta_B - \alpha + \Delta\theta_i$$

$$\theta_o = \theta_B + \alpha + \Delta\theta_o$$

$$\Delta\theta_i = -b\Delta\theta_o \quad (6)$$

Two assumptions can be made for the image formation model that is usually used in ABI when using SLS. First, in SLS-ABI, sources are placed quite a distance from the monochromator. Therefore, a point source and very little spatial blur can be assumed. Second, the radiation reflected by the monochromator is quasi-monochromatic and has an angular intensity profile (AIP) identical to the Darwin's curve.

According to the assumptions, when the analyzer and monochromator are perfectly aligned, the intensity detected after the analyzer (at the detector) is maximum. However, small rotations of the analyzer crystal produce partial overlaps of the two crystals' Darwin curves. The intensity of a particular alignment corresponds to a sample of the angular convolution of the Darwin curves, which is referred to as the rocking curve (RC):

$$RC(\theta, E) = r_o^m(\theta - \theta_B - \alpha, E) * r_i^a(\theta - \theta_B, E) \quad (7)$$

where $r_o^m$ and $r_i^a$ are the Darwin curves of monochromator and analyzer, respectively. When an object is placed between the two crystals, it distorts the RC as follows:

$$AIP(\theta) = I_0 \cdot RC(\theta, E) * f(\theta; E) \quad (8)$$

$$f(\theta; E) = \frac{\exp(-\mu(E))}{\sqrt{2\pi}\,\sigma(E)} \exp\left(-\frac{(\theta - \Delta\theta(E))^2}{2\sigma(E)^2}\right)$$

where $\mu$, $\Delta\theta$ and $\sigma$ are the absorption, refraction and scatter introduced by the object, which depend on the energy too. Also, $I_0$ is the total number of photons per pixel and AIP is the resulting angular intensity profile.

For simplicity, the DEI modality is often assumed. DEI uses two angular images ($I_L, I_H$) at the Full Width Half Maximum (FWHM) of the RC $\theta_L$, $\theta_H$, to estimate $\mu$ and $\Delta\theta$. To do so, DEI assumes a scatter free model, which simplifies equation (8):

$$f(\theta;E) = \exp(-\mu(E))\delta(\theta - \Delta\theta(E)) \Rightarrow AIP(\theta;E) \approx I_0 \cdot \exp(-\mu(E))RC(\theta - \Delta\theta(E);E) \quad (9)$$

where $\delta$ is Dirac's delta function. Additionally, DEI's model approximates AIP($\theta$,E) with its first order Taylor expansion at ($\theta_L$, $\theta_H$):

$$I_L(E) = \exp(-\mu(E))I_0\left(RC(\theta_L, E) + \Delta\theta(E) \cdot \frac{\partial RC}{\partial \theta}(\theta_L, E)\right) \quad (10)$$

$$I_H(E) = \exp(-\mu(E))I_0\left(RC(\theta_H, E) + \Delta\theta(E) \cdot \frac{\partial RC}{\partial \theta}(\theta_H, E)\right)$$

Under the model (10), in DEI absorption and refraction can be reconstructed as:

$$\mu_{DEI}(E) = \\ -\log\left(\frac{I_L(E) \cdot \frac{\partial RC}{\partial \theta}(\theta_H, E) - I_H(E) \cdot \frac{\partial RC}{\partial \theta}(\theta_L, E)}{RC(\theta_L, E) \cdot \frac{\partial RC}{\partial \theta}(\theta_H, E) - RC(\theta_H, E) \cdot \frac{\partial RC}{\partial \theta}(\theta_L, E)}\right) \quad (11)$$

$$\Delta\theta_{DEI}(E) = \frac{I_H(E) \cdot RC(\theta_L, E) - I_L(E) \cdot RC(\theta_H, E)}{I_L(E) \cdot \frac{\partial RC}{\partial \theta}(\theta_H, E) - I_H \frac{\partial RC}{\partial \theta}(\theta_L, E)}$$

Figure 4:
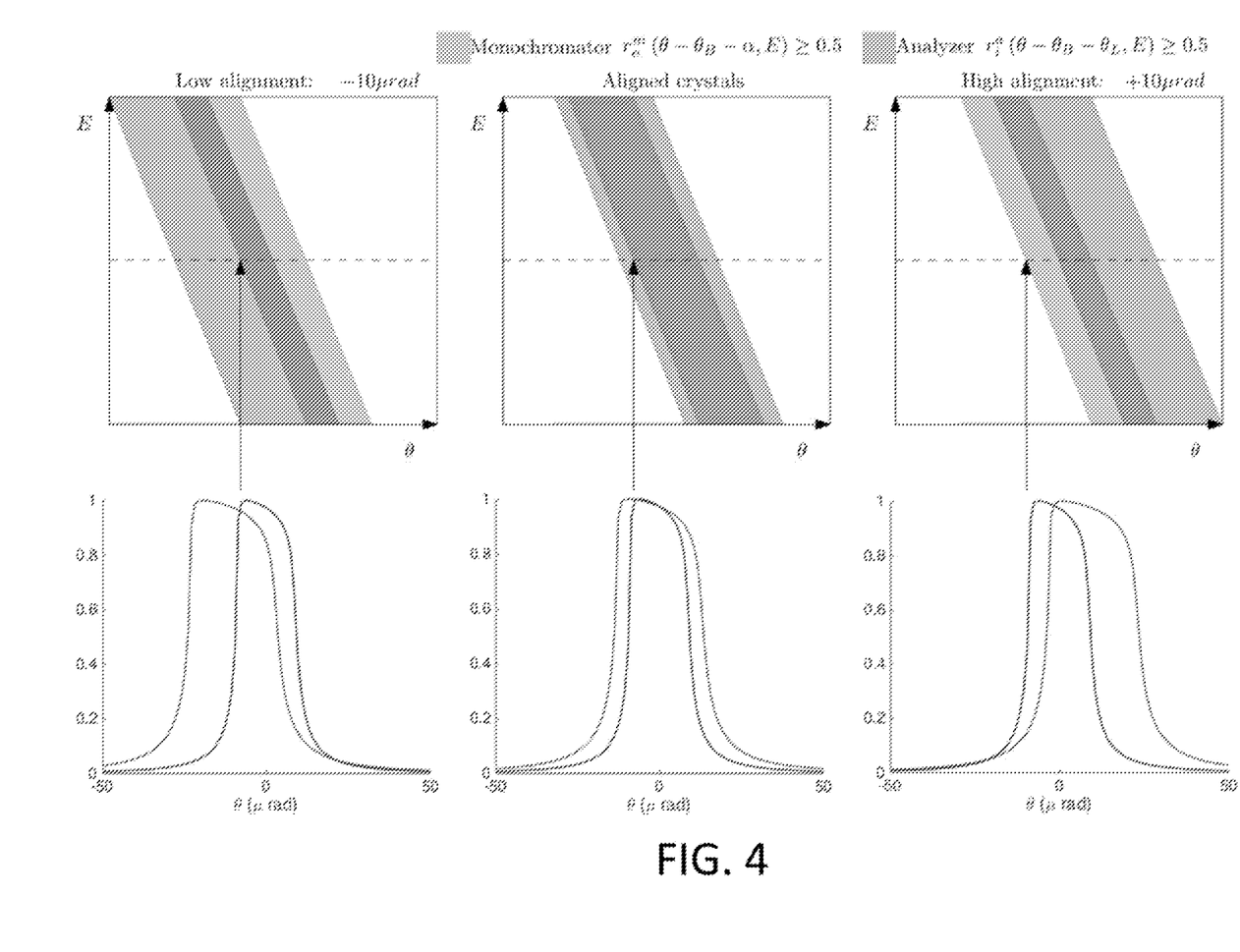
FIG. 4 depicts alignment of two Ge111 semiconducting crystals, and simultaneous alignment of all energies using an asymmetric monochromator. Shaded areas represent the combinations of angle and energy at which are reflected by the different crystals.

Referring to FIG. 3, due to Bragg's law, the energy range accepted in the crystal depends on the maximum and minimum angles at which a photon can arrive to the monochromator from the source. In general, since the source is closer to the monochromator, compact ABI setups of this invention accept a wider energy range than synchrotron systems. The photons with energy within this range are refracted only for small deviation of their Bragg's angle. As a result, after the monochromator, the energy across the beam is heavily correlated with the x coordinate. In particular, this phenomenon can be easily described using a DuMond diagram of the crystal. For example, FIG. 4 represents the reflectivity of a crystal for different energies and angles.

In order to use multiple energies for imaging, the analyzer and monochromator's DuMond diagrams need to be completely aligned. By using the same material and reflection plane for both crystals (i.e., Si111-Si111, Ge111-Ge111, etc.), both diagrams will always be overlapped, even when using an asymmetric monochromator (see FIG. 4). In such scenario, rocking the analyzer corresponds to a lateral shift in the analyzer's DuMond diagram. Ultimately, the analyzer acquires the rocking curve of the beam for all energies simultaneously, as visible in FIG. 4. Even though the energy content of the beam is different across the x-coordinate, ultimately, the whole sample interacts with all the energy range as it is scanned vertically through the beam.

In addition to accepting a wide energy range, compact ABI setups produce significant spatial blur due to the size of the source. However, if the spatial blur is ignored, the DEI angular images can be extended to the polychromatic case as:

$$\hat{I}_L = K \cdot I_0 \cdot \\ \int_{E_{min}}^{E_{max}} S(E)\exp(-\mu(E))\left(RC(\theta_L, E) + \Delta\theta(E) \cdot \frac{\partial RC}{\partial \theta}(\theta_L, E)\right)dE \quad (12)$$

$$\hat{I}_H = K \cdot I_0 \cdot \int_{E_{min}}^{E_{max}} S(E)\exp(-\mu(E)) \\ \left(RC(\theta_H, E) + \Delta\theta(E) \cdot \frac{\partial RC}{\partial \theta}(\theta_H, E)\right)dE$$

$$K = \left(\int_{E_{min}}^{E_{max}} S(E)dE\right)^{-1}$$

where S(E) is the source's energy spectrum and $\{E_{min}, E_{max}\}$ are the limits of the accepted energy range. From (12), the DEI estimator is computed using the experimentally measured polychromatic rocking curve, PRC($\theta$)=$K\int_{E_{min}}^{E_{max}}S(E)RC(\theta,E)dE$, as:

$$\hat{\mu} = -\log\left(\frac{\hat{I}_L \cdot \frac{\partial PRC}{\partial \theta}(\theta_H) - \hat{I}_H \cdot \frac{\partial PRC}{\partial \theta}(\theta_L)}{PRC(\theta_L) \cdot \frac{\partial PRC}{\partial \theta}(\theta_H) - PRC(\theta_H) \cdot \frac{\partial PRC}{\partial \theta}(\theta_L)}\right) \quad (13)$$

$$\Delta\hat{\theta} = \frac{\hat{I}_H \cdot PRC(\theta_L) - \hat{I}_L \cdot PRC(\theta_H)}{\hat{I}_L \cdot \frac{\partial PRC}{\partial \theta}(\theta_H) - \hat{I}_H \frac{\partial PRC}{\partial \theta}(\theta_L)}$$

However, if the RC is assumed to be symmetric $PRC(\theta) = PRC(-\theta)$, the resulting DEI parameters are:

$$\hat{\mu} = -\log\left(\frac{\int_{E_{min}}^{E_{max}} S(E)\exp(-\mu(E))RC(\theta_L E)dE}{\int_{E_{min}}^{E_{max}} S(E)RC(\theta_L E)dE}\right) \quad (13)$$

$$\Delta\hat{\theta} = \frac{\int_{E_{min}}^{E_{max}} S(E)\frac{\partial RC}{\partial \theta}(\theta_L, E)\exp(-\mu(E))\Delta\theta(E)dE}{\int_{E_{min}}^{E_{max}} S(E)\exp(-\mu(E))RC(\theta_L E)dE \cdot \frac{\partial}{\partial \theta}\int_{E_{min}}^{E_{max}} RC(\theta_L, E)dE}$$

Equation (13) corresponds to a weighted average of the attenuation and refraction across the accepted energy range. This is similar to common mammography or radiography, where a weighted absorption across the source's spectrum is measured.

For simplicity, a geometric approach is used to determine the maximum blur in the directions x and y. Additionally, a symmetric analyzer, big enough to fit the beam reflected by the monochromator, is assumed. Under quasi-monochromatic light conditions, the beam's angular divergence is determined by equation (6). An asymmetric crystal can increase the apparent distance $\hat{L}_1^{mono}$ between the source and the monochromator: $\hat{L}_1^{mono} = b^2 L_1$. As a consequence, the vertical magnification of a monochromatic system is:

$$M_v^{mono} = \frac{b^2 L_1 + L_2 + L_3}{b^2 L_1 + L_2} \quad (15)$$

As mentioned before, the samples are vertically scanned due to the reduced size of the beam. In order to scan the object continuously, the sample and detector movement are synchronized according to the magnification of the system. Specifically, the detector's speed is $M_v^{mono}$ times faster than the sample's speed: $v_d = M_v^{mono} v_s$. In the case of imaging at a synchrotron beam line, the source is located several meters away from the rest of the imaging system, producing very little magnification $M_v^{mono}$ 1 and, $v_d$, $v_s$. Unfortunately, equation (15) is only applicable to monochromatic radiation. Therefore, the vertical magnification for the polychromatic system is derived.

Figure 5:
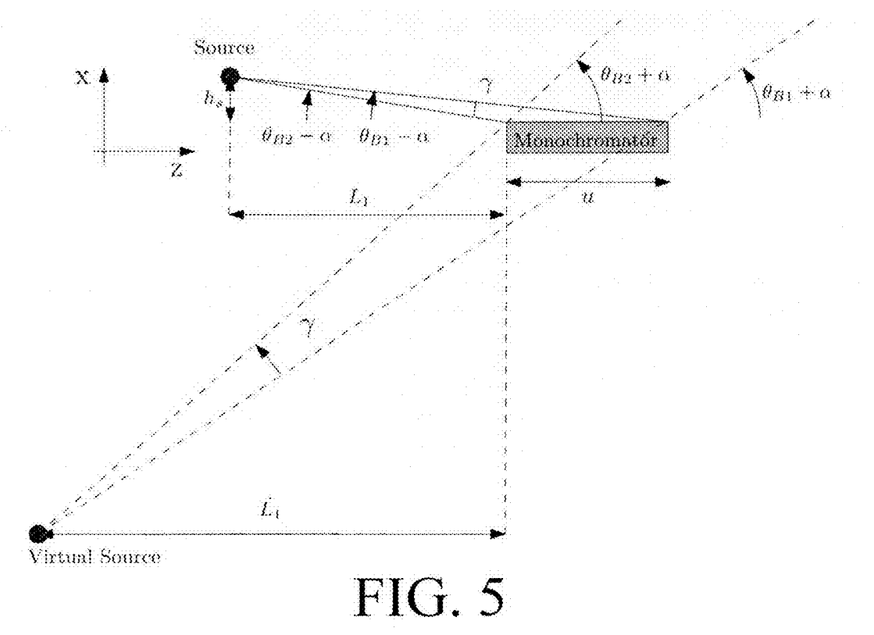
FIG. 5 depicts an apparent distance of the virtual source with an asymmetric monochromator and polychromatic light, according to one embodiment of this invention.

The apparent distance between the virtual source and the crystal $\hat{L}_1$ is measured. First, according to law of sines on the two triangles in FIG. 5:

$$\frac{\sin \gamma}{u} = \frac{\sin(\theta_{B1} - \alpha)}{L_1/\cos(\theta_{B2} - \alpha)} \quad (14)$$

$$\frac{\sin \gamma}{\mu} = \frac{\sin(\theta_{B1} + \alpha)}{\hat{L}_1/\cos(\theta_{B1} + \alpha)}$$

Next, the equations in (14) are combined, and with an approximation that $\cos(\theta_{B2}+\alpha)/\cos(\theta_{B2}-\alpha)$ 1, since $\theta_{B2} \pm \alpha$ are very small angles, results in:

$$\hat{L}_1 \frac{\sin(\theta_{B1} + \alpha)}{\sin(\theta_{B1} - \alpha)} L_1 = b\, L_1 \quad (15)$$

Using (15), the vertical magnification is:

$$M_v = \frac{b\, L_1 + L_2 + L_3}{b\, L_1 + L_2} \quad (16)$$

Figure 6:
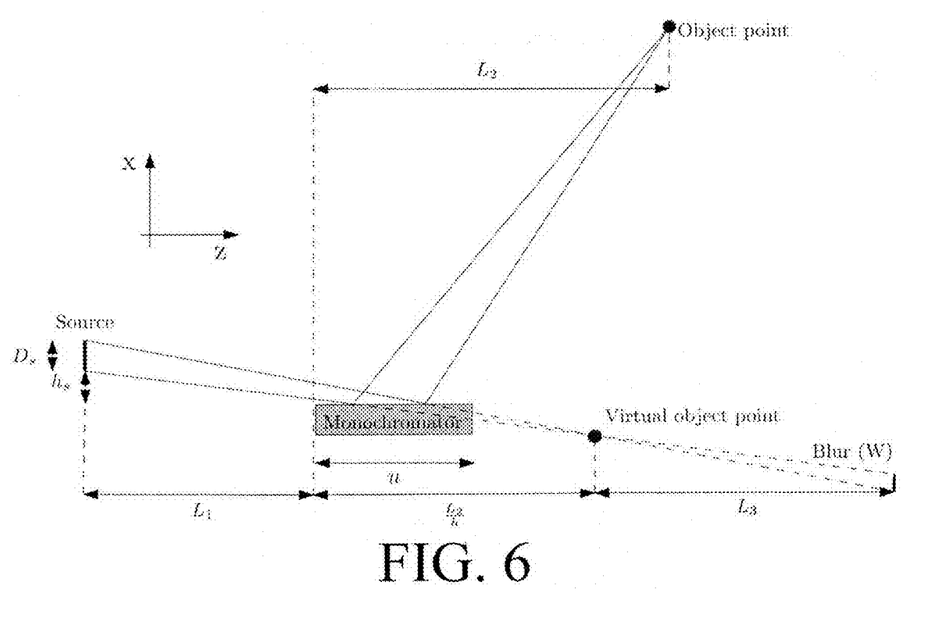
FIG. 6 depicts a virtual object point when using an asymmetric monochromator and polychromatic light according to one embodiment of this invention.

Similar to the magnification, the width of the vertical spatial blur of the system $W_v$ is derived by using the apparent crystal to object distance $L_2/b$ (see FIG. 6) as:

$$W_v = \frac{L_3}{L_1 + b^{-1}L_2} D_S = \frac{L_3}{bL_1 + L_2} bD_S \quad (17)$$

where $D_s$ is the source diameter. Finally, the vertical resolution of the system $\delta_v$ is evaluated by:

$$\delta_v = \frac{W_v}{M_v} = \frac{L_3}{bL_1 + L_2 + L_3} bD_S \quad (18)$$

All previous considerations refer to the vertical blurring and magnification. Regarding the horizontal spatial properties of the system, it can be studied as in regular mammography, since the system produces a fan beam:

$$M_h = \frac{L_1 + L_2 + L_3}{L_1 + L_2} \quad (19)$$

$$\delta_H = \frac{L_3}{L_1 + L_2 + L_3} D_S$$

As it can be seen in equations (18) and (19), the horizontal and vertical resolutions are the same if a symmetric crystals are used, b=1.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

To demonstrate the method and resulting images of this invention, a set of polystyrene cylinders using the Bremsstrahlung radiation of a tungsten-based source was imaged. The center of the beam was aligned using an Amptek XR-100T-CdTe spectrometer at 25 keV, where Tungsten sources present a smooth spectrum: no emission lines are present in the range.

Specifically, two experiments were performed using two different monochromators. In both cases the analyzer crystal was a symmetric Ge111. The first crystal was a 6 cm asymmetric Ge111 crystal polished at $\alpha=0.92°$. The monochromator was placed $L_1$=12.7 cm from the source and $L_2$=14.1 cm from the sample and the detector $L_3$=23.8 cm from the sample. The polystyrene phantom was imaged using continuous scanning with a relative speed derived from (16): Mv=1.7. Finally, a $D_s$=90 µm source was used with V=130 keV and I=458 µA. The reconstructed images can be observed in FIG. 7.

Figure 7:
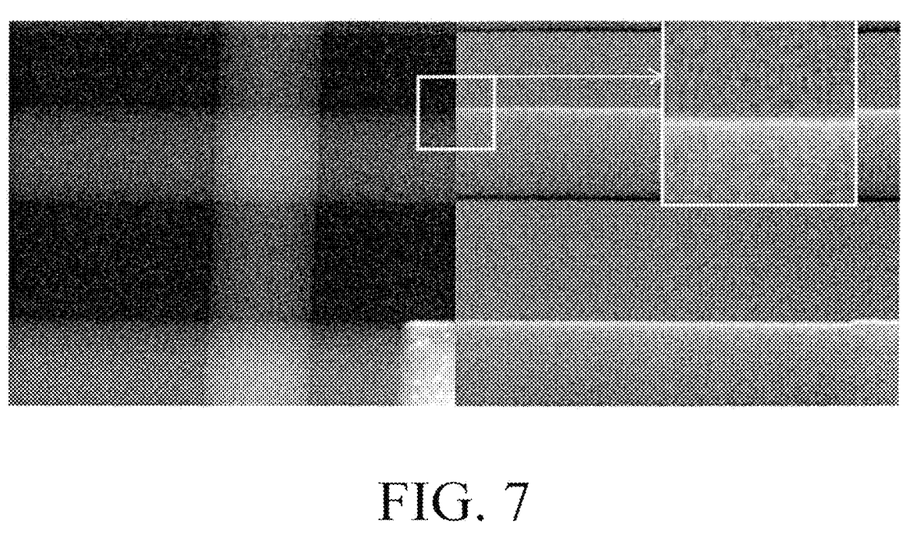
FIG. 7 depicts polystyrene rods imaged with Bremshtralung radiation (polychromatic light, 2 keV range) and continuous scanning.

FIG. 7 shows how a broad energy range can be used to obtain sharp images and confirms the derivation of the vertical magnification. The images in FIG. 7 5 were reconstructed to a pixel size of 25 µm on the object. A blur of approximately 2 pixels could be observed, corresponding to the spatial blur of $\delta_v$=55.7 µm.

Figure 8:
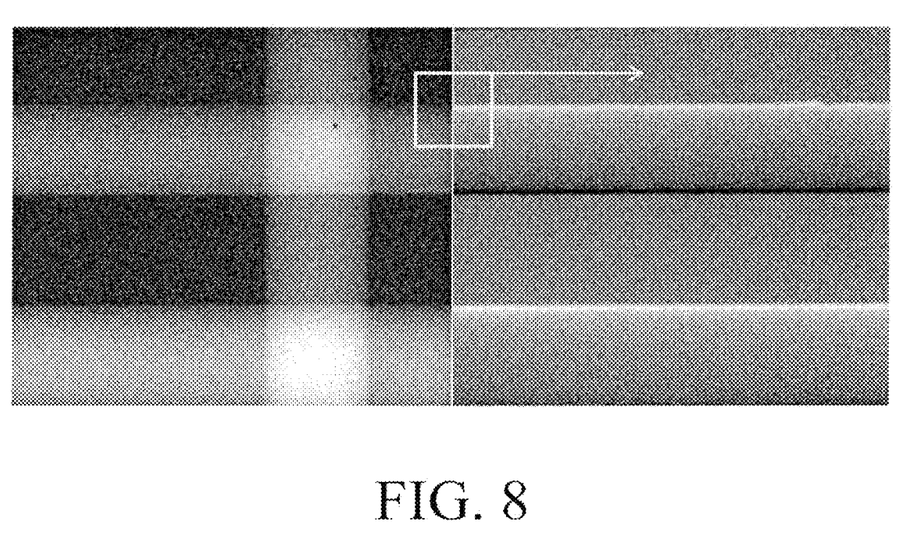
FIG. 8 depicts polystyrene rods imaged with Bremshtralung radiation (polychromatic light, 1.6 keV range) and continuous scanning.

The second crystal was a 2 cm asymmetric Ge111 polished at $\alpha$=1.6°. The system was setup with the following geometry: $L_1$=9.1 cm, $L_2$=15.0 cm, and $L_3$=23.5 cm. In this case, the vertical magnification was estimated to be $M_v$=1.66 and the source was setup at $D_s$=100 µm, V—130 kVm and I=500 µA. FIG. 8 shows the reconstructed images of the polystyrene rods. In this case, the theoretical spatial blur was 88.87 µm, which corresponds to the approximately 3-4 pixels in the image.

Figure 9:
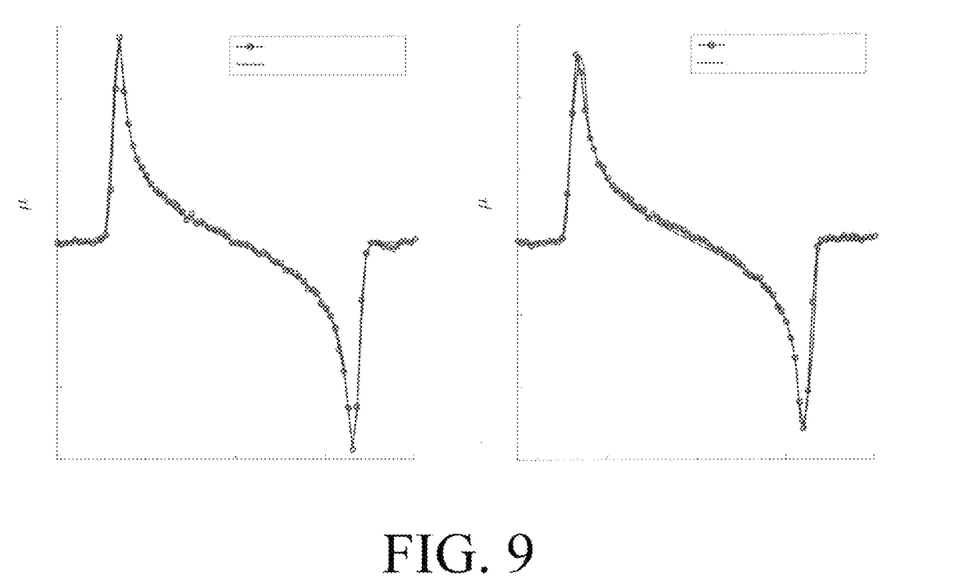
FIG. 9 depicts refraction image profiles of polystyrene cylinders (left: Rigaku crystal; right: Argonne crystal).

In order to further evaluate the theoretical model for the spatial resolution, the refraction profile of a polystyrene rod was simulated, which was evaluated as described:

$$\Delta\theta = \frac{\partial}{\partial x}\int \frac{r_e \lambda^2}{2\pi u}\rho(x,y,z)dz \quad (20)$$

where $r_e$ is the classical electron radius, u is the unified atom mass and $\rho$ is the polystyrene density distribution, which is known due to its regular cylindrical shape. Next, the model was blurred with a uniform kernel of size 55.7 µm and 88.87 µm for each of the images and the result was compared with the vertical profile of the refraction images, as shown in FIG. 9.

Figure 10:
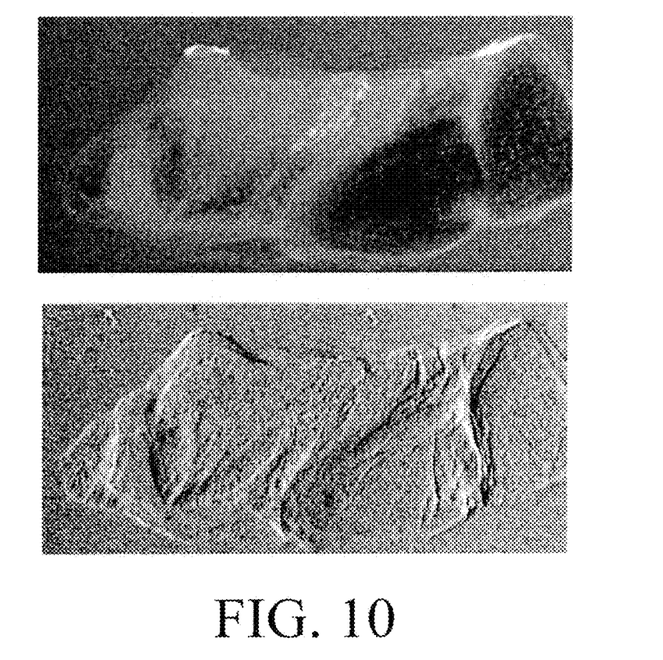
FIG. 10 depicts breast tumor tissue imaged with Bremshtralung radiation (polychromatic light, 2 keV range) and continuous scanning.

Finally, the first monochromator crystal was used with the same setup used before to image a breast tumor. FIG. 10 shows the reconstructed images of the sample.

The examples show the viability of the analyzer-based imaging techniques for wide-spectrum beams. Contrary to prior thought, quasi-monochromatic light is not necessary, especially if the same material crystals are used. The reconstructed images of the breast tumor show the level of detail achieved by ABI in the polychromatic mode.

In the past, double-crystal monochromators were limited the energy range of the system. Such designs absorb a lot of the radiation produced by the source. The experiments above show that a single crystal is enough. Alternatively to the double-crystal system, previous designs have tried to limit the size of the monochromator to reduce the energy range accepted in the system. However, given the results herein, there is no theoretical limitation on the crystal size. For instance, the biggest crystals currently commercially available are around 30 cm silicon pieces that could be used to produce substantially brighter beams for imaging and reduce the required exposure times significantly.

Thus the invention significantly relaxes design restrictions in compact ABI systems, by no longer requiring narrow energy range beams while still obtaining resolutions under 100 microns, which are necessary for applications such as mammography.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for detecting an image of an object in an analyzer-based system with a polychromatic x-ray beam from an x-ray source, wherein an analyzer crystal and a detector simultaneously acquire a rocking curve of the x-ray beam for all energies of the x-ray beam, the method comprising:
    diffracting the x-ray beam by an asymmetrical monochromator through the object; and
    synchronizing a detector movement with one of the x-ray source or the object.

2. The method of claim 1, further comprising moving the detector perpendicular to a longitudinal axis of the x-ray beam.

3. The method of claim 1, wherein the x-ray source is positioned 2 meters or less from the object.

4. The method of claim 1, wherein the synchronizing comprises the detector movement at a first rate that is different than a second rate of movement for the object or the x-ray source, and further comprising:
    detecting more than one image of the object at the detector during the synchronizing; and
    aligning the more than one image of the object as a function of a ratio of the first rate to the second rate.

5. A method for detecting an image of an object in an analyzer-based system with a polychromatic x-ray beam from an x-ray source, wherein an analyzer crystal and a detector simultaneously acquire a rocking curve of the x-ray beam for all energies of the x-ray beam, the method comprising synchronizing a detector movement with one of the x-ray source or the object, wherein the synchronizing comprises a detector movement at a first rate that is different than a second rate of the object or the x-ray source, wherein a ratio between the first rate and the second rate is determined by a magnification of the system.

6. The method of claim 5, further comprising diffracting the x-ray beam by an asymmetrical monochromator through the object.

7. The method of claim 5, wherein the synchronizing comprises moving the detector at a first rate that is faster than a second rate of the object or the x-ray source.

8. The method of claim 7, further comprising aligning more than one image of the object at the detector as a function of a ratio of the first rate to the second rate.

9. The method of claim 7, further comprising adjusting the first rate and/or second rate to improve a resolution of the image of the object.

10. The method of claim 7, wherein a ratio of the first rate to the second rate is a function of a vertical magnification of the analyzer-based system.

11. The method of claim 10, wherein the vertical magnification is a function of a crystal plane of a monochromator, a first distance between the x-ray source and a leading edge of the monochromator, a second distance extending from the leading edge to the object, and a third distance extending from the object to the detector.

12. A method for detecting an image of an object in an analyzer-based system, the method comprising:

generating a polychromatic x-ray beam from an x-ray source;
diffracting the x-ray beam by a monochromator;
transmitting the x-ray beam through the object and emitting from the object a transmitted beam;
directing the transmitted beam off a crystal analyzer to a detector;
synchronizing a movement of the object or the x-ray source with a detector movement during the transmitting, wherein the synchronizing comprises moving the detector at a first rate that is different than a second rate of the object or the x-ray source;
detecting more than one image of the object at the detector during the synchronizing;
aligning the more than one image of the object as a function of a ratio of the first rate to the second rate; and
combining the more than one image to derive the image of the object.

13. The method of claim 12, wherein the x-ray source is positioned 2 meters or less from the object.

14. The method of claim 12, further comprising adjusting the first rate and/or second rate to improve a resolution of the image of the object.

15. A method for detecting an image of an object in an analyzer-based system, the method comprising:
generating a polychromatic x-ray beam from an x-ray source;
diffracting the x-ray beam by a monochromator, wherein the monochromator comprises an asymmetric crystal;
transmitting the x-ray beam through the object and emitting from the object a transmitted beam;
directing the transmitted beam off a crystal analyzer to a detector;
synchronizing a movement of the object or the x-ray source with a detector movement during the transmitting;
detecting more than one image of the object at the detector during the synchronizing; and
combining the more than one image to derive the image of the object.

16. The method of claim 15, further comprising moving the detector perpendicular to a longitudinal axis of the x-ray beam.

17. The method of claim 15, wherein the synchronizing comprises moving the detector at a first rate that is different than a second rate of the object or the x-ray source.

18. A method for detecting an image of an object in an analyzer-based system, the method comprising:
generating a polychromatic x-ray beam from an x-ray source;
diffracting the x-ray beam by a monochromator;
transmitting the x-ray beam through the object and emitting from the object a transmitted beam;
directing the transmitted beam off a crystal analyzer to a detector;
synchronizing a movement of the object or the x-ray source with a detector movement during the transmitting, wherein the synchronizing comprises moving the detector at a first rate that is different than a second rate of the object or the x-ray source, and wherein a ratio of the first rate to the second rate is a function of a vertical magnification of the analyzer-based system;
detecting more than one image of the object at the detector during the synchronizing; and
combining the more than one image to derive the image of the object.

19. The method of claim 18, wherein the vertical magnification is a function of a crystal plane of the monochromator, a first distance between the x-ray source and a leading edge of the monochromator, a second distance extending from the leading edge to the object, and a third distance extending from the object to the detector.

20. An analyzer-based imaging system, comprising:
a polychromatic x-ray source in combination with an asymmetrical monochromator;
an analyzer crystal in combination with a detector;
an object holder between the monochromator and the analyzer crystal; and
a controller configured to synchronize a detector movement with one of the x-ray source or the object holder.

21. The system of claim 20, wherein the controller is configured to move the detector at a first rate that is different than a second rate of the object holder or the x-ray source.

* * * * *